United States Patent [19]

Young

[11] Patent Number: 5,662,596
[45] Date of Patent: Sep. 2, 1997

[54] TRUE BI-PIVOTAL ORTHOPEDIC AND ORTHOTIC HINGE WITH INCREMENTAL MOTION CONTROL

[76] Inventor: David Ernest Young, Bowler's Piece, 16 Couching Street, Watlington, Oxfordshire, OX9 500, United Kingdom

[21] Appl. No.: 521,547

[22] Filed: Aug. 30, 1995

[51] Int. Cl.[6] ........................................... A61F 5/01
[52] U.S. Cl. ..................................... 602/26; 602/16
[58] Field of Search ............................. 602/16, 26

[56] References Cited

U.S. PATENT DOCUMENTS

| | | | |
|---|---|---|---|
| 4,239,524 | 12/1980 | Anderson | 128/80 C |
| 4,520,802 | 6/1985 | Mercer et al. | 602/16 |
| 4,697,583 | 10/1987 | Mason et al. | 128/80 C |
| 4,732,143 | 3/1988 | Kausek et al. | 602/16 |
| 4,881,299 | 11/1989 | Young et al. | 16/371 |
| 4,881,532 | 11/1989 | Borig et al. | 128/80 A |
| 4,915,098 | 4/1990 | Young et al. | 128/88 |
| 4,940,044 | 7/1990 | Castillo | 602/16 |
| 5,000,170 | 3/1991 | Young et al. | 128/80 C |
| 5,038,765 | 8/1991 | Young et al. | 602/16 |
| 5,039,247 | 8/1991 | Young et al. | 403/92 |

FOREIGN PATENT DOCUMENTS

| | | |
|---|---|---|
| 1299455 | 4/1992 | Canada . |
| 0 301 817 | 1/1989 | European Pat. Off. . |
| 0 327 286 | 9/1989 | European Pat. Off. . |
| 615734 | 9/1994 | European Pat. Off. ............ 602/16 |
| 88/5584 | 6/1989 | South Africa . |
| 2182714 | 5/1987 | United Kingdom . |
| 2207458 | 2/1989 | United Kingdom . |
| 2208065 | 2/1989 | United Kingdom . |

Primary Examiner—Richard J. Apley
Assistant Examiner—David R. Risley
Attorney, Agent, or Firm—Tilton Fallon Lungmus

[57] ABSTRACT

The hinge has optimally spaced pivots in which extension and flexion travel of each independently pivoted hinge arm is limited by a series of planar metal stops acting on both arms and in both directions. Each stop has first and second pairs of angled stop faces for limiting extension at optionally different angles and first and second pairs of angled stop faces for limiting flexion at optionally different angles. The hinge arms are disposed between a front plate and a back plate and pivot means for each hinge arm also serve as securing means securing the plates and hinge arms together. Each stop is secured by a single screw which passes through one plate. Stops are mounted in the internal flexion angle of the hinge.

7 Claims, 3 Drawing Sheets

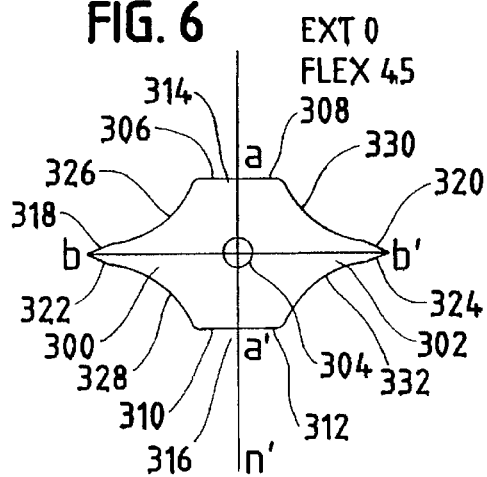
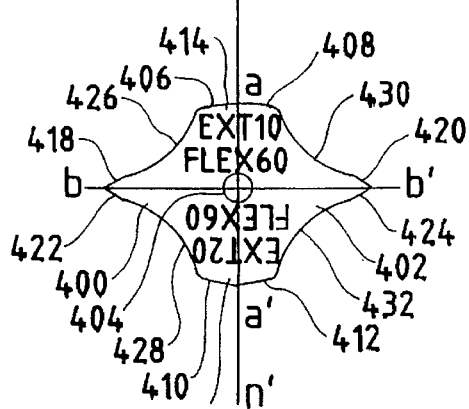
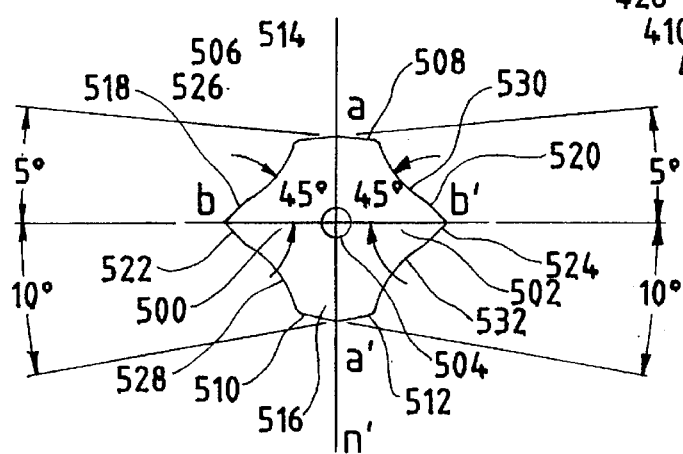
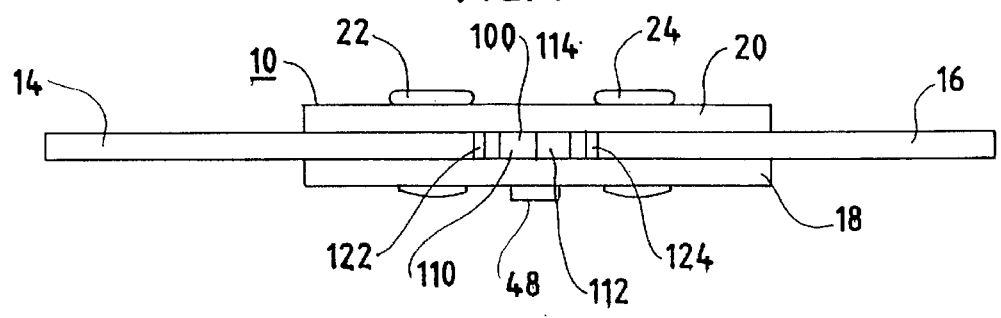

TRUE BI-PIVOTAL ORTHOPEDIC AND ORTHOTIC HINGE WITH INCREMENTAL MOTION CONTROL

FIELD OF THE INVENTION

This invention relates to hinges employed in orthoses and orthopedic braces used on the human body, particularly the knee joint. In particular, the invention relates to novel means for limiting the flexion and extension travel of the arms of a true bi-pivotal hinge.

BACKGROUND OF THE INVENTION AND THE PRIOR ART

There are many hinge designs used in orthopedic splints and braces employed at the knee.

In a first widely used type, there are two hinge arms joined at and flexing about a single pivot. This type is generally referred to by those skilled in the art as the uni-axial, uni-pivotal or monocentric type.

In a second type, perhaps even more widely used, there are two hinge arms each having its own pivot and also each having a set gear teeth about the periphery of the part which extends between the pivots. The arms are so sized and arranged that the gear teeth mesh between the pivot points thereby integrating the arm movements. Thus if one arm moves, the other must move as well. This type is generally referred to by those skilled in the art as the geared bi-axial, geared duocentric or geared polycentric type. The latter term is perhaps the most widely recognized.

Neither of these hinge types is remotely physiological in the way they move and because their mechanical action is so unlike that of the human knee their use in a brace construct may be positively deleterious to an injured, repaired or deformed knee.

The term brace construct is used by those skilled in the art to describe the resultant mechanical arrangement of a brace and the leg to which it is attached. A combination of casting materials (such as Plaster of Paris or resin impregnated bandages) and cast bracing hinges as well as braces secured on the leg by means such as straps are brace constructs once they are in place on the leg.

Mechanically, the knee is a modified, crossed, four bar linkage comprising the rigid elements femur, tibia and the anterior and the posterior cruciate ligaments. Its axis of rotation moves backwards or posteriorly as the knee is flexed from the fully extended position. The locus or track of the axis of knee rotation is called the "Instant Center Pathway" which exactly defines the moving path of the center of knee rotation at any given instant. Uni-axial and geared polycentric hinges do not have this construction; they do not move in this manner and within a brace construct they cannot accommodate or track the complex motion of the knee properly.

Another type of hinge design used in orthopedic splints and braces employed at the knee has two hinge arms each having its own pivot but in this design there are not gear teeth. Thus, in this type, the arm movements are not integrated and each arm can always move independently without affecting the other. This type of hinge is generally referred to by those skilled in the art as the true bi-axial, true bi-pivotal or simply just bi-pivotal type. It continues to grow in popularity with the realization that such a construction is superior to the others in providing the freedom necessary to accommodate the complex and changing locus of the axis of the knee throughout the entire flexion/extension cycle.

Both bi-pivotal hinges and geared polycentric hinges are, in mechanical terms, three bar linkages. However, the geared integration of the hinge arms in the geared polycentric type arms causes the loss of one degree of freedom. When used in most orthopedic braces both types require at least one stop at or near the fully extended position to prevent over-travel of the knee into hyperextension. In bracing and general orthopedic and orthotic applications a three bar linkage hinge mechanism, with all degrees of freedom available, offers the most practical and appropriate mechanical arrangement for accommodating the complex motion of the knee.

The present author has been concerned for many years with research and development of bi-pivotal hinges based upon pivot spacings between 24 mm and 30 mm. When such hinges are used as part of a brace construct, the net rearward travel of the instant center pathway of the knee axis which can be accommodated approximates to that which is likely to be encountered in the great majority of patients. This was confirmed at Sheffield and Brunel Universities in the United Kingdom in 1986 and 1987.

In addition it was confirmed, in 1984, by means of combined video, computer and force-plate gait analysis, that when used at the knee, bi-pivotal hinges with such pivot spacings introduce less disturbance to the normal gait (or walking pattern), than either geared polycentric two-pivot hinges or uni-axial hinges. Furthermore, it has been shown that pistoning and zig-zagging does not occur in such hinges (provided they are fitted properly) when the knee is under load. This work was carried out at Derby Royal Infirmary, Derby, United Kingdom in 1984 and was presented at the 8th World Orthopaedic Congress in Washington, DC, USA, May 4–10, 1987 by Dr. David Pratt. Dr. Pratt's principal co-author was David Rowley, M.D., F.R.C.S., now Professor of Orthopaedics and Trauma Surgery, The University, Dundee, Scotland.

By way of contrast, if geared polycentric hinges are restrained at a point along each hinge arm some distance from each pivot and flexed, they are driven forwards in the opposite direction to natural knee motion. In a brace construct this is exactly the form of restraint applied, usually by sets of securing straps above and below the knee. This movement is easy to demonstrate in a brace not in place on a leg. However, in a brace construct movement is substantially prevented by the securing straps and the net effect is to generate forces which act counter to the flexing forces generated by the flexor muscle groups acting on the knee. The opposite effect is encountered during extension of the knee in such a brace construct and in both cases, the resolution of these extraneous forces is through a compromised knee joint.

It is possible, by altering the architecture of a geared polycentric hinge, to partially alleviate these effects. This can be done, for instance, by introducing a substantial anterior displacement of the femoral hinge arm and a substantial posterior displacement of the tibial hinge arm and arranging the gearing accordingly. Such an arrangement is taught in U.S. Pat. No. 4,697,583 to Mason et al., assigned to Don Joy Orthopedic Inc. of Carlsbad, Calif., USA.

Another concern to those who have to set up and adjust braces is the total number of parts to be handled when a brace needs adjustment. This is a particular problem with braces which have incremental extension and flexion stop. In every commercially available system known to the present author which employs incremental stops, extension stops and flexion stops are secured separately by at least one screw for each stop and there is often a hinge cover which has to be removed as well. This is the case with a 1995 released product from Don Joy Inc. of Carlsbad, Calif., and called "Legend"™ which is admittedly a geared polycentric device. In this product, two screws on each hinge release a hinge cover, a flexion stop and an extension stop. To make any change, at least two further stops must be selected and handled from a choice of four different extension stops (8 in total) and four different flexion stops (8 in total).

This calls for a minimum of four screws, two hinge covers and four stops (two outgoing and two incoming)—10 parts plus the selection of two of these from a minimum of eight—to be handled at any given stop change. This level of handling is not particularly unusual in prior art braces but it is very time consuming.

However, the present invention is concerned solely with art of bi-pivotal hinges and further references to the prior art will be so restricted. The present author has been the first inventor of a number of adjustment mechanisms for true bi-pivotal hinges providing continuously variable stops. These are described in patents GB 2 182 714 and U.S. and EPO counterparts U.S. Pat. No. 4,915,098 and 327286, respectively, U.S. Pat. No. 5,000,170 and Canadian counterpart 1 299 455; GB 2 208 065 and U.S. counterpart U.S. Pat. No. 4,881,299 and U.S. Pat. No. 5,039,247.

A series of patents to Borig et al. is relevant to continuously variable stops in bi-pivotal hinges and comprises UK 2 207 458 and counterparts U.S. Pat. No. 4,881,532, EPO 301817, AUS 79761 and SA 88/5584.

In addition, the present author is first inventor of U.S. Pat. No. 5,038,765 which discloses selectable "T"-shaped inserts with abutment stops for limiting angular travel of one movement of both arms of a true bi-pivotal hinge. As generally disclosed, this movement is extension, which is undoubtedly the most usual movement which would be required to be controlled. However, claim 1 is not limited to extension and it is clear that flexion, alone, could also be limited as taught. In such a flexion limiting implementation, separate means for at least preventing hyperextension, would necessarily have to be included.

A brace embodying these inserts for limiting extension travel has been sold for several years, by leading companies, including recently by Johnson and Johnson Professional of Raynham, Mass., and Bracknell, Berkshire, United Kingdom in a number of countries, including the United Kingdom and the United States. The product is sold under the commercial name Masterbrace™ and is manufactured by Protectair Limited, Abingdon, Oxfordshire, United Kingdom.

The present author is aware of few other commercially available examples of true bi-pivotal hinges and has found few relevant references in the art via patent and commercial literature searches.

In recent years a great deal of attention has been paid by those skilled in the art to the design of functional knee braces which are intended to provide stability for unstable knees. current opinion favors designs in which hinges are disposed in close approximation to the knee, have minimal thickness profiles and generally offer limited control of extension and flexion.

Accordingly, continuously variable stop mechanisms are now mainly found in rehabilitation braces which are used immediately following injury or repair to knee ligaments and are otherwise generally simpler braces. In those patients at a later stage of rehabilitation and returning to active sport, discontinuous or incremental stop mechanisms are acceptable in the functional knee braces typically prescribed at that stage.

A functional knee brace known to have been made and sold by Messrs. Omni Scientific of Martinez, Calif., is believed to be based on Anderson, U.S. Pat. No. 4,249,524. This teaches a true bi-pivotal hinge; however, the pivots are very widely spaced. It seems inevitable that, in such a hinge, shortening would occur during flexion, leading to effective shortening of a cast or brace in which it was used. Such shortening would allow the injured or recently repaired knee joint to piston and to experience undesirable loads.

In the Anderson patent, the hinge center bar apparently fulfills the function of both a mounting for the pivots and for the hinge arms since it extends to a position where members, normally termed headplates or limb bands, would be employed.

For instance, in a functional knee brace intended for use by a person returning to active contact sport following a ligament injury, there is an expectation, not always justified, that the brace will provide physical protection for the knee. If wide pivotal spacing is employed on the lateral hinge, the medial collateral ligament will receive little, if any, protection from the brace if a substantial, medially directed, lateral blow is suffered when the knee is moderately flexed.

Although Anderson briefly mentions stops, no motion control system is disclosed in any detail. In any such system, the inter-relationship between the control of motion and the pivot spacing in true bi-pivotal hinges is of paramount importance.

Directly relevant is U.S. Pat. No. 4,520,802 to Mercer and Aaserude which teaches another bi-pivotal cast bracing hinge featuring wide pivot spacing. These authors disclose a motion control system based preferably upon multiple indexing blocks.

As written, the intention seems to be to provide mainly flexion control for a true bi-pivotal hinge on at least one flex bar (frequently termed a hinge arm by other authors). FIGS. 1 and 5 support this view since it is clear in these drawings that extension is limited only by the fundamental provision of hyperextension stop means represented by element 23. The specification is confusing in that element 5 is described as a support bar or rod but in FIGS. 1 and 4 it appears to be illustrated as a screw or pin structure which might be means of limiting extension but which is not described as such.

Dispositions of the indexing blocks are disclosed both beyond and between the pivots although claim 1 is limited to the latter position. It is certainly not possible to envisage any method or means within the scope of this disclosure by which more than one flex bar could be controlled by one index block if it were disposed beyond one pivot. It is also very difficult to envisage how closely spaced pivots could be employed if two index blocks were disposed between the pivots.

The detailed description states, in column 6 at line 27, a preference for a pair of index blocks, thereby contemplating the use of a single structure. No means is actually taught for accomplishing this and it is neither clear nor obvious from any part of the disclosure how this might be achieved. In claim 1, the authors refer to a structure involving a pair of index blocks and it is clear that these are intended to be used together and disposed between the pivots.

For instance, in FIG. 1, there is shown an arrangement of two indexing blocks disposed between the pivots, necessitating a minimum distance between the pivots of two indexing block widths, plus an allowance for the ends of the flex bars sufficient to create a flexion stop on each and leaving sufficient metal about the pivots to ensure structural integrity and durability. In such a case, the argument applied to wide spacing in relation to the Anderson patent op cit applies. In FIG. 5, where two indexing blocks are disposed outside the pivots, there is no need for the wide spacing shown but one block could not control both pivots.

In addition, it seems clear from drawings 1 and 5b and the detailed description, that the authors did not contemplate the provision of both flexion stops and extension stops on one indexing block. It also seems at least likely that the means for providing extension was intended to be conveyed by a description of element 5, the description of which as a "support bar or rod" duplicates the description of element 1.

In the structure as disclosed, it would be impossible to fit a single indexing block, even with extension stops, since the broadest dimension of such a block would have to be introduced through a narrower dimension between those portions of the flex arms extending between the pivots, in order to reach and act upon on the extension surfaces of the flex bars which come to rest against the back of center bar element 23.

With two indexing blocks, intended to offer extension stops, the pivot spacing would have to be widened still further to allow introduction of both blocks and this would, in any case, be physically difficult. Once again the general argument applied to wide spacing would detract from the usefulness of such a hinge.

FIG. 3, in conjunction with the paragraph commencing at line 36 of column 6 seems to indicate clearly the authors' intentions, namely that the second class of face designated 14, abuts the back of center bar 23 (FIG. 1) locking index block 3 in position whichever flexion stop face is selected. If this condition is fulfilled, it becomes geometrically impossible to incorporate flexion stop faces and extension stop faces together within a single index block 3. This applies regardless of whether one or two are used, in any rational orthopedic or orthotic hinge device. The provision of structural element 23 appears crucial to the implementation of index blocks as taught by Mercer and Aaserude.

SUMMARY OF THE INVENTION

The present invention provides a true bi-pivotal hinge, for orthopedic and orthotic braces used on the human body and particularly at the knee, which has an improved incremental motion limiting mechanism.

In the invention, a true bi-pivotal hinge is provided with a series of novel, more or less diamond-shaped, interchangeable, metal, combined extension and flexion insert stops. Each insert stop body provides at least one and optionally two different angular settings for extension limitation and at least one and optionally, two different angular settings for flexion limitation. In this novel arrangement it is not necessary to have any part of the insert stop accommodated and disposed between the extreme ends of the hinge arms between the pivots.

The arrangement of the invention allows the instant hinge to have narrow pivot spacing in the range 24 mm to 30 mm, which is the optimal arrangement for a true bi-pivotal hinge. This is because the modified, crossed, four-bar linkage mechanism of the human knee has an instant center pathway which tracks posteriorly as the knee travels from full extension to full flexion by a similar distance. Such an unconstrained bi-pivotal hinge, which is a three-bar linkage, offers excellent practical accommodation, during flexion and extension motion, of the complex motion of the knee's four-bar linkage mechanism. This is accomplished without the introduction of extraneous forces associated with the use of uni-axial and geared polycentric hinges.

In this invention, there is no requirement for a structure within or formed by the hinge body to lock the stop in place after it has been secured in place. Each diamond-shaped insert stop is secured by a single screw which passes through either the front plate or back plate of the hinge. This feature, together with the optional plurality of different extension stop angles and optional plurality of different flexion stop angles provided on each insert stop allows quicker, easier and more economical adjustment of angular hinge arm travel than is achievable with prior art extension and flexion stops mechanisms for bi-pivotal hinges.

The ease of use of the instant invention is further enhanced by the geometric structure which allows a pair of extension stop faces not in use to be employed as a tab or handle for introducing that pair which is required into the hinge body. The insert stop body may also be held in the correct position by this means whilst the securing screw is placed and driven home.

According to the invention, there is provided a true bi-pivotal hinge, with narrow pivot spacing, for use in orthopedic and orthotic braces which has a series of single, flat, interchangeable, incremental insert stops made in suitable metals such as titanium or stainless steel and which are secured in the flexion angle of the hinge.

According to the first aspect of the invention, the incremental metal insert stops have a first pair of angled extension stop faces, one for each independently pivoted hinge arm, each face being disposed at half the total extension stop angle required.

According to the second aspect of the invention, the incremental metal insert stops have a second pair of angled extension stop faces, one for each independently pivoted hinge arm, each face being disposed at half a total extension stop angle required and optionally differing from the first extension stop angle by a clinically useful increment.

According to a third aspect of the invention, the incremental metal insert stops have a second pair of angled flexion stop faces, one for each independently pivoted hinge arm, each face being disposed at half the total flexion stop angle required.

According to a fourth aspect of the invention, the incremental metal insert stops have a second pair of angled flexion stop faces, one for each independently pivoted hinge arm, each face being disposed at half a total flexion stop angle required and optionally differing from the first extension stop angle by a clinically useful increment.

According to a fifth aspect of the invention, each interchangeable metal insert stop body is secured by a single screw which passes non-threadedly through either a front plate or back plate of the hinge body and which is received threadedly into the stop body.

According to a sixth aspect of the invention, the end portion of each approximately diamond-shaped insert stop having the pair of angled extension stop faces not selected may be used as a handle or grip for introducing the selected pair of angled extension stop faces into the hinge body at the time of fitting or removal.

According to a seventh aspect of the present invention, each insert stop body is provided with markings which clearly indicate the total angular values of each pair of flexion and extension stops.

It is, therefore, the principal object of this invention to provide a true bi-pivotal hinge for use in orthopedic and orthotic braces having narrow pivot spacings, preferably disposed apart by a distance measurement between centers in the range 24 mm to 30 mm and provided with a series of interchangeable, flat, metal, more or less diamond-shaped insert stops each offering a plurality of paired extension stops and a plurality of paired flexion stops for limiting extension and flexion travel of both the hinge arms.

It is another important object of this invention to provide a series of insert stops each offering first and second pairs of angled extension stop faces, each angled face within each pair being intended to cooperate with one independently pivoted hinge arm and also being disposed at half a total extension stop angle required. Additionally, the total extension stop angle presented by the first pair of extension stop faces optionally differs from that presented by the second pair of extension stop faces by a clinically useful angular increment.

Other objects and advantages will become clear as the present invention is described in greater detail, by way of example only, with reference to the accompanying drawings.

BRIEF DESCRIPTION OF THE DRAWINGS

In general, a convention of describing the position of structural elements in drawings in relation to their anatomical disposition has been adopted using terms such as 'anterior' and 'posterior' to describe fore and rear with respect to a human body upon which the device of the instant invention would be applied.

FIGS. 6, 7 and 8 are front or lateral views of further combined extension and flexion insert stop configurations according to the present invention.

FIG. 9 is a posterior view of a hinge according to the present invention with a combined extension and flexion insert stop in place.

DETAILED DESCRIPTION OF PREFERRED EMBODIMENTS

Figure 1:
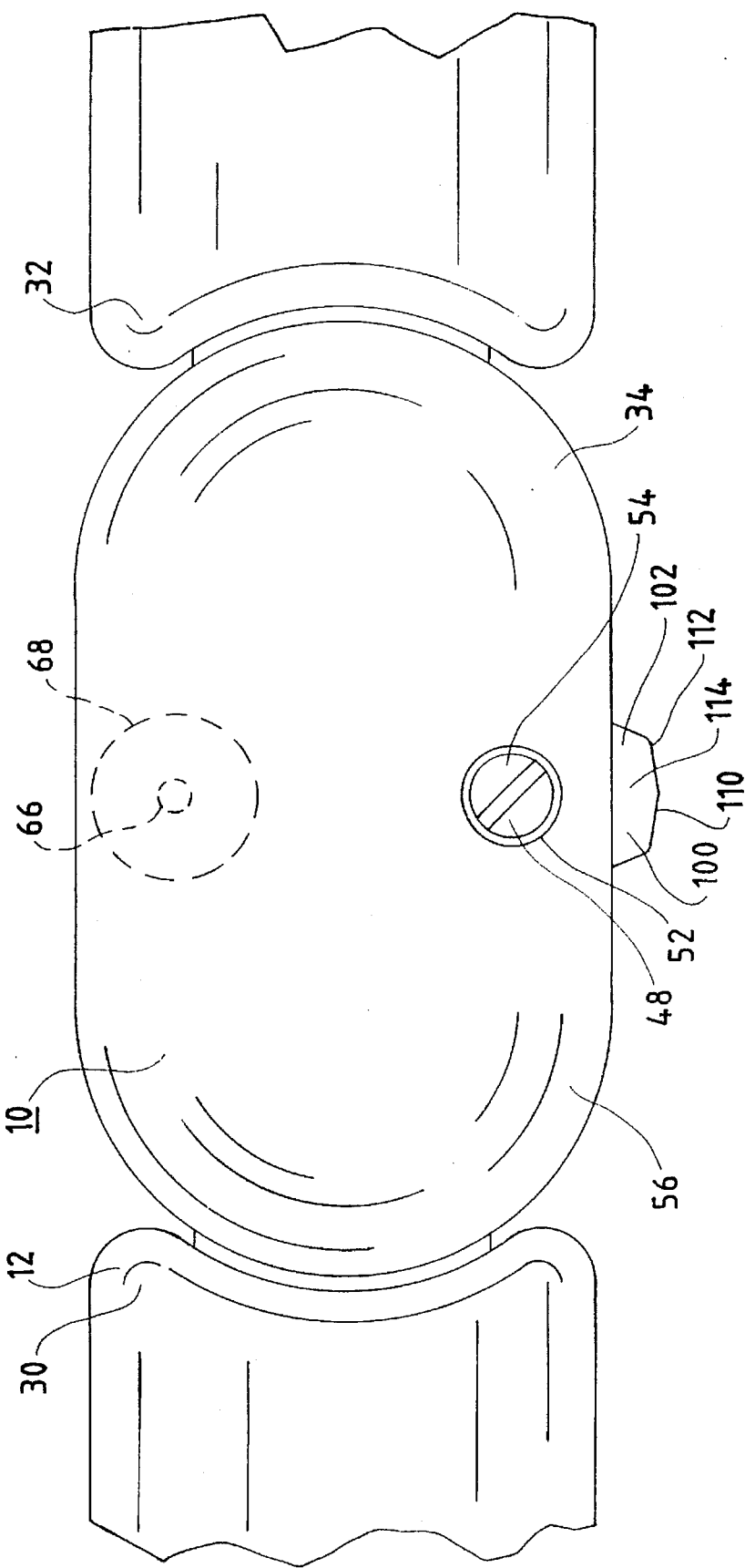
FIG. 1 is a lateral front view of an orthopedic knee brace fitted with a fully assembled true bi-pivotal hinge according to the present invention.

With general reference to FIGS. 1–9, a true bi-pivotal hinge according to a preferred embodiment of the present invention, has the general designation 10 and is generally represented as part of an orthopedic knee brace 12. It is to be understood that hinge 10 will generally but not always, be used in a paired configuration with one such structure being disposed medially and the other laterally with respect to the human knee. Hinge 10 comprises the major structural elements first and second substantially flat hinge arms 14 and 16, a substantially flat front plate 18 and a substantially flat back plate 20. These elements are conventionally made in metals such as aluminum or titanium. As described, hinge 10 is not a handed structure.

Figure 2:
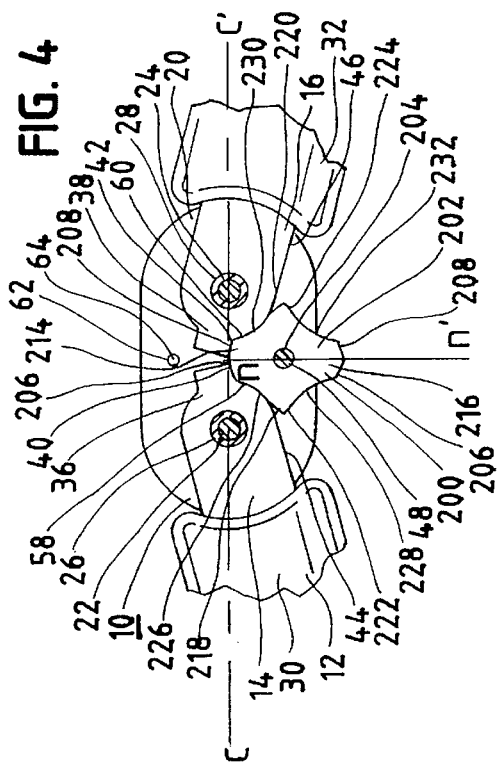
FIG. 2 is a lateral front view of part of an orthopedic knee brace fitted with a true bi-pivotal hinge with the hinge cover and front plate partly cut away to show part of a first combined extension and flexion insert stop according to the present invention. The hinge arms are shown extended against the stop.
Figure 3:
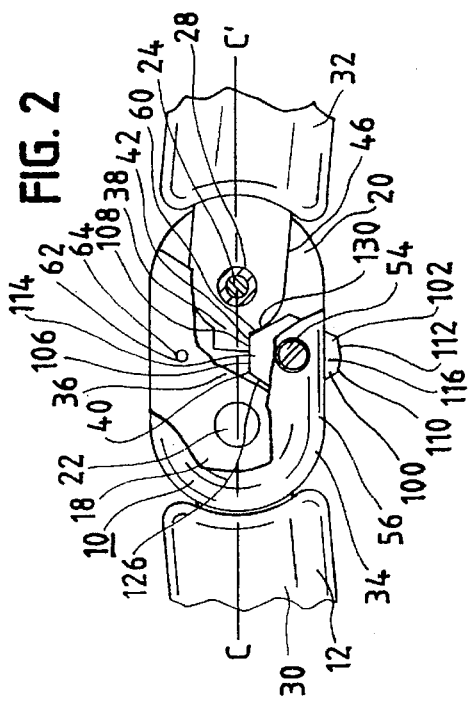
FIG. 3 is a lateral front view of the instant hinge with the hinge cover and front plate removed to show a second view of a first combined extension and flexion insert stop with the hinge arms flexed against the stop.
Figure 4:
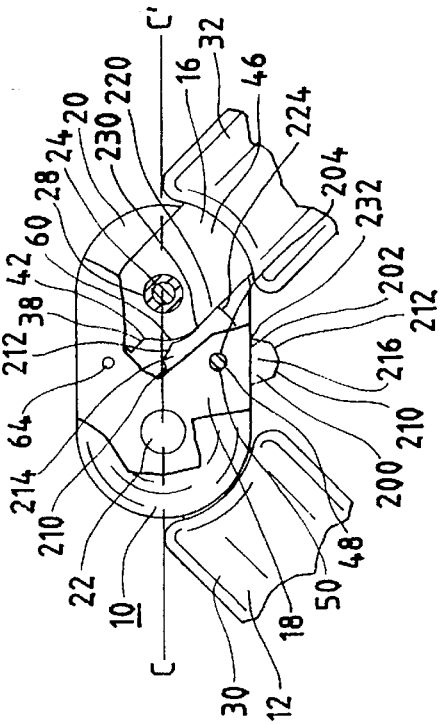
FIG. 4 is a lateral front view analogous to FIG. 3 showing a first view of a second combined extension and flexion insert stop according to the present invention. The hinge arms are shown extended against the insert stop.

Front plate 18 and back plate 20 are disposed in a parallel relationship and hinge arms 14 and 16 are disposed between them, each being independently pivotally mounted upon pivot rivet axis means 22 and 24 (shown in section in FIGS. 2–5) provided with bushing means 26 and 28 (28 is shown in section in FIGS. 2–5; 26 is shown in section in FIGS. 3 and 4). The spacing between the centers of 22 and 24 is strongly preferred to be in the range 24 mm–30 mm.

In the embodiment illustrated, hinge arms 14 and 16 are overmolded in a suitable soft but durable material such as an injection molding grade of synthetic rubber indicated at 30 and 32. Additionally, hinge 10 has a front cover 34, conveniently made in molded plastics. The first purpose of overmolds 30 and 32 and hinge cover 34 is to ensure that metal parts do not impinge upon the person of the wearer and also if the device were to be used in contact sports to protect another participant. A second purpose is to enhance the cosmetic appearance. Hinge cover 34 has a further purpose which will be described, in context, below.

Each of hinge arms 14 and 16 has an extension 36 and 38 which extends beyond and between pivot rivets 22 and 24, respectively but which neither interdigitates with nor touches the other. Posterior edges 40 and 42 of extensions 36 and 38 and the non-overmolded posterior edges 44 and 46 of hinge arms 14 and 16 which lie disposed between front plate 18 and back plate 20, constitute abutment faces. Abutment faces 40 and 44 lie in the same plane and when hinge arm 14 is in full extension these faces are also parallel to a line c——$c^1$ between pivot rivet axis means 22 and 24.

Abutment faces 40, 42, 44 and 46 cooperate with corresponding structures, described below, provided by each and every one of a series of approximately diamond-shaped combined extension and flexion insert stops. Five insert stops in such a series are illustrated and are designated 100, 200, 300, 400 and 500. However, it is to be understood that whilst some of these insert stops are typical of those which may commonly be used, they represent only a few of the possible combinations which may be made or required in a rational clinical range from full extension or 0° to about 130° flexion.

Combined extension and flexion insert stop 100 has a structure which is typical of the series. It is planar and made of suitable metals, such as titanium or stainless steel and has a thickness substantially the same as hinge arms 14 and 16. Insert stop 100 has a stop body 102 provided with a threaded hole 104. Threaded hole 104 provides means by which insert stop 100 is secured, threadedly, by screw 48 (shown in section in FIGS. 3–5) to and against front plate 18 and hinge cover 34. Front plate 18 has a hole 50 (seen only in FIG. 5) for receival, non-threadedly, of screw 48 with minimal clearance. Hinge cover 34 has a tapered recess 52, centrally positioned in which is a hole (not seen) also for receival, non-threadedly, of screw 48. When screw 48 is driven fully home, its head 54, lies just under flush with the surface 56 of hinge cover 34.

Figure 5:
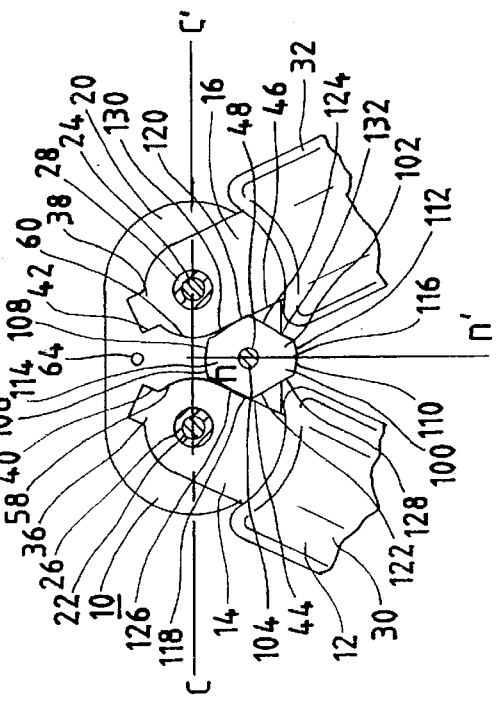
FIG. 5 is a lateral front view analogous to FIG. 2 but with slightly different parts of the hinge cover and front plate cut away and a showing a second view of part of a second combined extension and flexion insert stop according to the present invention. The hinge arms are shown flexed against the insert stop.

As may be seen by reference to FIGS. 3, 4 and 5, the center of hole 50 in front plate 18 is located on a line n–$n^1$ normal to and running posteriorly from center line c–$c^1$. This line also bisects the distance between the centers of pivots 22 and 24. The position of hole 50 is selected to optimize the geometrical solutions applied to the selection of insert stops.

As may be seen by brief reference to FIGS. 6–8, insert stops are symmetrical about an axis a–a¹ which runs from the apex of the first total extension stop angle to the apex of the second total stop angle. Insert stops are not necessarily symmetrical about an axial line b–b¹ drawn between the apices of angles between adjacent flexion stop faces. However, the position of the center of the threaded securing hole illustrated at 104, 204, 304, 404 and 504 in the drawings always lies at the intersection of lines a–a¹ and b–b¹.

Insert stop geometry will be strongly influenced by the required stop angles selection but other factors, such as the width of hinge arms 14 and 16, the shape and position of extensions 36 and 28 and the overall shape and size of hinge body 10 and its other major components, are important.

For clarity lines a–a¹ and b–b¹ will be referred to in the general text, hereinafter, as "vertical apical axis" and "horizontal axis", respectively.

In insert stop 100 each member 106, 108 of a first pair of extension stop faces is symmetrically disposed either side of a vertical apical axis at an angle of 5° to and above a horizontal axis, thus presenting, as illustrated in FIG. 2, a total extension stop angle of 10° to abutment faces 40 and 42 of extensions 36 and 38 of hinge arms 14 and 16, respectively. Each member 110, 112 of a second pair of extension stop faces is also symmetrically disposed either side of the vertical apical axis at an angle of 10° to and below the horizontal axis, thus providing, when required, a second total extension stop angle of 20° for abutment faces 40 and 42.

As best seen in FIG. 1 at enlarged scale, that part 114 of stop body 102 which is adjacent to stop faces 110, 112 also functions as a tab or handle. This feature is useful when changing entire insert stops or switching stop values. For instance, in order to use the second pair of extension stop faces 110, 112 and provide hinge 10 with 20° of extension block, screw 48 is removed and stop 100 is readily withdrawn using handle 114. Insert stop 100 is then reversed and handle 116, which is the equivalent part of stop body 102 adjacent to stop faces 106, 108 (seen in FIGS. 2 and 3) is used to introduce extension stop faces 110, 112 into the correct position within hinge 10. Handle 116 may also be used to hold insert stop 100 in position while screw 48 is relocated and driven home. Provided hinge arms 14 and 16 are extended and flexed against insert stop 100 before screw 48 is fully tightened, stop 100 will center itself and line up properly without the need for secondary adjustment of its position.

In insert stop 100 each member 118, 120 of a first pair of flexion stop faces is symmetrically disposed either side of the vertical apical axis at an angle of 65° to and above the horizontal axis. This arrangement presents, as illustrated in FIG. 3, a total flexion stop angle of 130° to abutment faces 44 and 46. Each member 122, 124 of a second pair of flexion stop faces is also symmetrically disposed either side of the vertical apical axis at an angle of 65° to and below the horizontal axis thus also providing a total flexion stop angle of 130° for abutment faces 44 and 46.

Radii 126, 128, 130 and 132 all have the same dimension, which is somewhat greater than the radium of curved portions 58 and 60 of hinge arms 14 and 16. This arrangement is to ensure clearance between insert stop 100 and hinge arms 14 and 16 at all positions of hinge arm travel between selected extension stop faces and selected flexion stop faces. These radii are all tangential to a circle centered upon the intersection of axes a–a¹ and b–b¹. This confers the basic diamond-shape upon the central body portion of all insert stops. The radii add concavity to the sides and the stop selection superimposed upon this basic architecture dictates the final shape which varies considerably within the overall basic diamond pattern.

Thus, single combined extension and flexion insert stop 100, located in the net flexion angle of hinge 10 offers extension blocking at 10° and 20° each with, effectively full flexion. This is a rational and desirable set of combinations for a knee in the later stages of rehabilitation following surgical repair to a ruptured anterior cruciate ligament (ACL). A healthy knee, without a brace fitted, may well flex beyond 130° but with a brace in place, above and below knee structures thereof will generally impinge upon one another at large flexion angles. In any case, insert stops according to the present invention may readily be made with any required flexion angle value.

Combined extension and flexion insert stop 200 is analogous to insert stop 100 and has the equivalent structures 202–232. If differs only in that extension stop faces 206, 208 are symmetrically disposed either side of the vertical apical axis at an angle of 15° to and above the horizontal axis and presents, as illustrated in FIGS. 4 and 5, a total extension stop angle of 30° to abutment faces 40 and 42. Also, extension stop faces 210, 212 are symmetrically disposed either side of the vertical apical axis at an angle of 20° to and below the horizontal axis providing, when required, a second total extension stop angle of 40° for abutment faces 40 and 42. Both total flexion stop angles are 130°, as in insert stop 100.

Combined extension and flexion insert stops 300, 400 and 500, shown isolated in FIGS. 6–8, are also analogous to insert stop 100 and have the equivalent structures 302–332, 402–432 and 502–532. These insert stops are included to allow a discussion of the rationale for stop selection and of apparent limits of the diamond pattern architecture related to materials selection.

In FIG. 6, insert stop 300 has first and second pairs of extension stop faces 306, 308, 310, 312. Both pairs provide an extension stop angle of 0°, which is full extension. Insert stop 300 also has first and second pairs of flexion stop faces 318, 320; 322, 324 both of which offer a flexion stop angle of 45° for abutment faces 44 and 46.

Insert stop 300 is not truly rational under the present invention, an important advantage of which is to provide multiple combinations of extension and when required, flexion as well. It is included because it represents a worst-case scenario for the instant insert stops when under load. As seen in FIG. 6, insert stop 300 has narrow left and right extremities in the region of flexion stop faces 318, 320 and 322, 324, respectively. A 45° flexion stop setting is a most unlikely selection in a modern functional bracing based treated regime for late rehabilitation following ACL or other ligamentous reconstruction and is outside the present author's experience. Furthermore, as discussed in the preamble, braces used earlier in the post-operative phase are usually preferred with continuous control of flexion and extension. Nonetheless, it is not wished to limit the invention and it is for this reason that the insert stops are recommended to be made in the preferred metals. With such metals used in thicknesses likely to be preferred for hinge arm construction, tests have shown that insert stops configured as in 300 are adequate to withstand forces likely to be encountered during use.

In FIG. 7, insert stop 400 represents a more rational but still rather unusual combination in which the first pair of extension stop faces 406, 408 present a total extension stop angle of 10° and the second pair of extension stop faces 410, 412 present a total extension stop angle of 20°. Both pairs of flexion stop faces 418, 420; 422, 424 present a total flexion stop angle of 60°. This insert stop is mainly included to indicate, by comparison with FIG. 6, that the amount of stop material available to support compression loads in flexion increases rapidly with increasing flexion stop angle. Insert stop 400 in FIG. 7 is shown with suitable preferred markings. The convention of marking each portion of a stop with the setting it actually has rather than those of the opposite end, is preferred as less confusing.

In FIG. 8, insert stop 500 represents a rational combination in which the first pair of extension stop faces 506, 508 present a total extension stop angle of 10° and the second pair of extension stop faces 510, 512 present a total extension stop angle of 20°. Both pairs of flexion stop faces 518, 520; 522, 524 present a total flexion stop angle of 90°. This insert stop is also included partly to indicate further, by comparison with FIGS. 6 and 7, that the amount of stop material available to support compression loads in flexion increases rapidly with increasing flexion stop angle. FIG. 8 shows both pairs of extension stop face angles and one pair of flexion stop face angles of stop 500 labeled.

In all the examples illustrated, with the exception of insert stop 300 in FIG. 6, combination stops have two extension blocking angles and one flexion blocking angle. This reflects the fact that in practice during later stages of rehabilitation of the knee, there is a greater and more frequent requirement to revise extension blocking rather flexion blocking. Those charged with the care of patients, therefore, will often prefer to have to make less decisions about flexion (which they will in any case choose to set at full flexion) and have several combinations of extension stop immediately available which involve minimal stop changes.

An advantage of the present invention is that in such a scenario, which is very likely, a carer would need only two insert stops for each hinge. Each insert stop would have both sets of flexion stops providing 130° of flexion block. One insert stop would offer extension blocking at 10° and 20°—as illustrated with respect to stop 100 in FIGS. 2 and 3. The other insert stop would offer extension blocking at 30° and 40°. Such an approach reduces handling of insert stops and associated parts and thereby saves time.

Obviously a responsible manufacturer would include with a brace incorporating a hinge or hinges according to the present invention, a sufficient range of insert stops to cover all common clinical circumstances and make others available as required. In fact such a basic range, covering most needs would probably be configured as follows:

|  | Extension First Pair | Extension Second Pair | Flexion First Pair | Flexion Second Pair |
| --- | --- | --- | --- | --- |
| Stop 1 | 0° | 0° | 130° | 90° |
| Stop 2 | 10° | 20° | 130° | 130° |
| Stop 3 | 30° | 40° | 130° | 130° |
| Stop 4 | 10° | 20° | 60° | 90° |

Expressed differently, an orthopedic brace according to the present invention and provided with such a set of insert stops would allow adjustment to:

| Full extension | with 90° or 130° of flexion |
| --- | --- |
| 10° extension block | with 60° or 130° of flexion |
| 20° extension block | with 90° or 130° of flexion |
| 30° extension block | with 130° of flexion |
| 40° extension block | with 130° of flexion |

This range, providing 8 combinations from insert 4 stop entities, would cover most if not all requirements from early middle to late rehabilitation in a functional knee brace, even where a surgeon favors a "straight-through" approach. This involves using a functional knee brace throughout treatment, eschewing the use of a traditional so-called rehabilitation brace during the post-operative period and thereby reducing costs.

In contrast, the incremental stop system disclosed by the present author in U.S. Pat. No. 5,038,765 and applied in the commercial product Masterbrace™, described earlier, uses four insert stops to achieve four variations of extension block with only full flexion being allowed. Worse cases are cited in the prior art.

In the present invention, hinge cover 34 is secured from behind hinge 10 by a self-tapping screw 62 (shown in section in FIGS. 2 and 5). Self-tapping screw 62 passes non-threadedly through a clearance hole 64 in back plate 20 and engages self-threadingly with a blind pilot hole 66 in a boss 68 (both shown in hidden detail in FIG. 1). This feature makes it unnecessary to remove or in any other way handle hinge cover 34 during an incremental insert stop change. In addition, since only a single screw 48 secures the combination extension and flexion insert stops of the present invention, the maximum number of parts which need to be handled is much less than in prior art systems. For instance, a typical insert stop change on a two-sided functional knee brace where extension block is altered will involve handling only two screws and two insert stops—four parts in all. There is a good chance no new insert stop entities will be needed; however, even if they are needed, the total number of parts to be handled still only rises to six—40% less handling than that required in the 1995 geared polycentric hinge product cited in the prior art statement.

Finally, the provision of combination extension and flexion insert stops which feature the advantage of handles deserves some further discussion.

In general, prior art incremental insert stops are difficult to introduce, remove and secure and this adds to handling time and slower patient throughout. The stop handles provided by the present invention and exemplified by 114 and 116 in insert stop 100 overcome this problem. It might be argued that their protrusion beyond the posterior edge of the hinge body is disadvantageous. However, those skilled in the art will recognize that a protrusion which is maximally about 6 mm by an unselected 40° extension stop (the maximum likely to be encountered) into the posterior, flexion angle of the hinge, is most unlikely to be troublesome.

Any such insert stop is likely to have a 30° flexion stop as its selected functional partner. No patient wearing a functional or other orthopedic knee brace so configured, would or could participate in contact sports.

In contrast, insert stops according to the present invention, with full extension provided by both first and second pairs of extension stop faces, are likely to be used by those who participate in contact sports. However, these insert stops will protrude only about 3 mm into the posterior, flexion angle of the hinge which is an insignificant hazard. Brief reference to FIG. 1, which is at enlarged scale, will indicate how little insert stop 100 protrudes, even with the 10° extension block engaged and the 20° extension block functioning as a handle.

In a second embodiment (not illustrated) all the crucial structures of the first embodiment are identical except that there is no hole 48 in hinge cover 34. Instead, insert stops are secured by an identical screw passing non-threadedly through a non-threaded hole in back plate 20 which corresponds to hole 50 in front plate 18 of the first and preferred embodiment. This screw is received into a tapered recessed hole in an inner hinge cover which corresponds to 52 of hinge cover 34 of the first and preferred embodiment. Such an embodiment might be preferred if it were felt that patients would interfere with the insert stop retaining screw. However, such a screw citing would be impossible to access with the brace on the patient and this would detract from some of the advantages of the invention relating to time saving.

Whilst the present invention has been described in respect of particular embodiments, modifications may readily be made by those skilled in the art. It is intended that the claims should cover any such modifications falling within the spirit and scope of the invention.

I claim:

1. An orthopedic bi-pivotal hinge comprising a hinge body having a pair of plates defining a space therebetween; two hinge arms having extended adjacent end portions located in said space and independently pivotally connected to said plates for pivotal movement of said each arm in directions of extension and flexion independent of the other of said arms; and a generally diamond-shaped insert element removably secured between said plates having a central body portion and a plurality of corners with a pair of angularly-oriented stop faces adjacent to each corner; said pairs of stop faces constituting abutment surfaces; each said hinge arm being engagable with one of said surfaces for limiting the extent of pivotal movement in extension and being engagable with the other of said surfaces for limiting the extent of pivotal movement in flexion said body portion being generally coplanar with said hinge arms and extending partially therebetween; and connecting means removably securing said body portion of said insert element to said hinge body.

2. The hinge of claim 1 in which said body portion of said insert element has a single opening therein; said connecting means comprising a single screw element securable to said plates and extending through said opening for releasably securing said insert element within said space.

3. The hinge of claim 1 in which said abutment surfaces are each disposed at a selected angle within the range of 0°–65° measured from a line passing through the two pivot axes of said bi-pivotal hinge.

4. The hinge arm of claim 3 in which two of said abutment surfaces are on opposite sides of an apical line perpendicular to a line passing through both of said pivot axes and being located with said apical line spaced equidistant from said pivot axes; said abutment surfaces being at the same angle relative to said line passing through said two pivot axes.

5. The hinge of claim 1 in which a second generally diamond-shaped insert element is provided; said second insert element being interchangeable with said first-mentioned insert element and differing from said first-mentioned insert element essentially by a difference in the angular orientation of each pair of said stop thereof.

6. An orthopedic and orthotic bi-pivotal hinge comprising a body having a front plate and a back plate disposed in parallel relation and defining a space therebetween; two hinge arms having adjacent end portions located in said space and independently connected to said body along two spaced pivot axes for independent movement of each arm in directions of and flexion; said end portion of each hinge arm having a longitudinal extension defining a first posterior edge portion providing an extension-limiting abutment face; each hinge arm having a second posterior edge portion spaced from said first posterior edge portion and defining a flexion-limiting face; a generally diamond-shaped insert element removably secured to said body within said space said insert element being symmetrical about an apical axis perpendicular to a line passing through both of said pivot axes and being located with said apical axis spaced equidistant from said pivot axes; said insert element providing a pair of extension-limiting stop faces on opposite sides of said apical axis with each said stop face being engagable with said first posterior edge portion of a hinge arm for limiting the angle of extension of said arm; said insert element also providing a pair of flexion-limiting faces along opposite sides of said apical axis with each said flexion-limiting stop face being engagable with said second posterior edge portion of a hinge arm for limiting the angle of flexion of said arm.

7. The hinge of claim 6 in which said insert element has a single opening therein; said connecting means comprising a screw element securable to said side walls and extending through said opening for releasably securing said insert element within said space.

* * * * *